(12) United States Patent
Kohara (10) Patent No.: US 9,816,932 B2
(45) Date of Patent: Nov. 14, 2017

(54) PULSED LIGHT SYNCHRONIZER AND MICROSCOPE SYSTEM

(71) Applicant: CANON KABUSHIKI KAISHA, Tokyo (JP)

(72) Inventor: Naoki Kohara, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/313,420

(22) PCT Filed: Aug. 13, 2015

(86) PCT No.: PCT/JP2015/004045
§ 371 (c)(1),
(2) Date: Nov. 22, 2016

(87) PCT Pub. No.: WO2016/027444
PCT Pub. Date: Feb. 25, 2016

(65) Prior Publication Data
US 2017/0184504 A1   Jun. 29, 2017

(30) Foreign Application Priority Data

Aug. 18, 2014   (JP) ................... 2014-165643

(51) Int. Cl.
*G01N 21/25*   (2006.01)
*G01N 21/65*   (2006.01)
(Continued)

(52) U.S. Cl.
CPC ......... *G01N 21/65* (2013.01); *G02B 21/0032* (2013.01); *G02F 1/3534* (2013.01);
(Continued)

(58) Field of Classification Search
CPC ........ G01N 21/68; G01N 21/64; G01N 21/65; G01J 3/44; G02B 21/05; G02B 21/00; H01S 3/13; H01S 3/23
See application file for complete search history.

(56) References Cited

U.S. PATENT DOCUMENTS 3,925,727 A * 12/1975 Duguay ............... G01R 13/347
250/227.12
8,629,980 B2   1/2014 Ozeki et al.
(Continued)

FOREIGN PATENT DOCUMENTS

JP   11-084438 A   3/1999
JP   2010-097063 A   4/2010
(Continued)

OTHER PUBLICATIONS

Ozeki, et al., "Stimulated Raman scattering microscope with shot noise limited sensitivity using subharmonically synchronized laser pulses", Jun. 21, 2010.

*Primary Examiner* — Abdullahi Nur
(74) *Attorney, Agent, or Firm* — Fitzpatrick, Cella, Harper & Scinto (57) ABSTRACT

A pulsed light synchronizer synchronizes a first pulsed light having a first period and a second pulsed light and having a second period equal to the first period with each other. A third pulsed light is acquired by providing a first delay time between two pulsed lights acquired by dividing the first pulsed light, and by multiplexing the pulsed lights acquired from the first pulsed light. A fourth pulsed light is acquired by providing a second delay time between two pulsed lights acquired by dividing the second pulsed light, and by multiplexing the pulsed lights acquired from the second pulsed light. The pulsed light synchronizer detects, through a detector, a pulsed light acquired by multiplexing the third and fourth pulsed lights, and adjusts at least one of the first and (Continued)

second periods based on a timing difference between the third and fourth pulsed lights acquired from the detector.

13 Claims, 4 Drawing Sheets

(51) Int. Cl.
*G02B 21/00* (2006.01)
*H01S 3/13* (2006.01)
*H01S 3/23* (2006.01)
*G02F 1/35* (2006.01)

(52) U.S. Cl.
CPC .............. *H01S 3/13* (2013.01); *H01S 3/2391* (2013.01); *G01N 2021/655* (2013.01); *G01N 2201/0697* (2013.01); *G01N 2201/06113* (2013.01); *G01N 2201/105* (2013.01)

(56) References Cited

U.S. PATENT DOCUMENTS

| | | | |
|---|---|---|---|
| 9,103,726 | B2 | 8/2015 | Ozeki et al. |
| 9,109,954 | B2 | 8/2015 | Ozeki et al. |
| 2010/0232459 | A1 | 9/2010 | Hashimoto et al. |
| 2011/0080580 | A1 | 4/2011 | Fermann et al. |

FOREIGN PATENT DOCUMENTS

| | | | |
|---|---|---|---|
| JP | 4862164 | B2 | 1/2012 |
| JP | 2013/507005 | A | 2/2013 |
| JP | 2014-507627 | A | 3/2014 |
| JP | 5501360 | B2 | 5/2014 |
| WO | 2007/132540 | A1 | 11/2007 |
| WO | 2010/140614 | A1 | 12/2010 |
| WO | 2012/121920 | A2 | 9/2012 |
| WO | 2013/084621 | A1 | 6/2013 |

\* cited by examiner

THIRD PULSED LIGHT

[Fig. 2B]

FOURTH PULSED LIGHT
(IN SYNCHRONIZATION STATE)

[Fig. 2C]

TWO-PHOTON ABSORPTION
SIGNAL
(IN SYNCHRONIZATION STATE)

[Fig. 2D]

FOURTH PULSED LIGHT
(LATER THAN
SYNCHRONIZATION STATE)

$\Delta t1 < \Delta t2$

[Fig. 2E]

TWO-PHOTON ABSORPTION
SIGNAL(LATER THAN
SYNCHRONIZATION STATE)

[Fig. 2F]

FOURTH PULSED LIGHT
(FASTER THAN
SYNCHRONIZATION STATE)

$\Delta t1 > \Delta t2$

[Fig. 2G]

TWO-PHOTON ABSORPTION
SIGNAL(FASTER THAN
SYNCHRONIZATION STATE)

[Fig. 3]

OUTPUT VOLTAGE FROM SYNCHRONOUS DETECTION CIRCUIT 12

TIMING DIFFERENCE BETWEEN PULSES

FIRST PULSED LIGHT

[Fig. 5B]

THIRD PULSED LIGHT
(PULSE TIMING
SYNCHRONIZATION STATE)

FIRST PULSED LIGHT

[Fig. 7B]

SECOND PULSED LIGHT

PULSED LIGHT SYNCHRONIZER AND MICROSCOPE SYSTEM

TECHNICAL FIELD

The present invention relates to a pulsed light synchronizer and a microscope system that synchronize timings of two pulsed lights (or pulsed light trains) emitted from two pulsed lasers.

BACKGROUND ART

In a nonlinear optical microscope, such as a stimulated Raman scattering microscope, configured to exploit a nonlinear optical process, pulsed lights emitted by two pulsed lasers need to be focused on a sample with timings of their pulses being synchronized (or a difference between the timings being kept constant).

PLT 1 discloses a stimulated Raman scattering (SRS) microscope that detects, as a pulse timing difference, an output from a photodetector that detects two-photon absorption and adjusts a pulse period so that the detected value is equal to a set value. PLT 2 discloses a coherent anti-Stokes Raman scattering (CARS) microscope that adjusts a pulse period based on a difference between outputs from two photodetectors used to detect a pulse timing difference.

CITATION LIST

Patent Literature

[PLT1] Japanese Patent No. 5,501,360
[PLT2] Japanese Patent No. 4,862,164

SUMMARY OF INVENTION

Technical Problem

In PLT 1, when the light intensities, wavelengths, and pulse durations of the pulsed lights are changed, outputs from the photodetector and an output circuit thereof need to be set to different values to achieve equivalent pulsed light synchronization accordingly, but PLT 2 can achieve the pulsed light synchronization without such setting. However, PLT 2 requires such a configuration that the two photodetectors have the same sensitivity with the same wavelength characteristic, and lights input to the photodetectors have the same light intensity and pulse duration. Otherwise, the pulsed light synchronization cannot be achieved, and pulses of the pulsed lights emitted from the two pulsed lasers have a timing difference when the wavelengths are changed. Moreover, since an output from a photodetector largely depends on the arrangement of a focusing objective lens and a light-receiving surface of the photodetector, the two photodetectors need to have identical arrangements relative to the objective lens.

The present invention provides a pulsed light synchronizer and a microscope system that can reliably operate.

Solution to Problem

A pulsed light synchronizer as an aspect of the present invention synchronizes a first pulsed light produced on a first period and a second pulsed light produced on the first period with each other. The pulsed light synchronizer includes a first delay multiplexer configured to produce a third pulsed light by providing a first delay time between two pulsed lights acquired by demultiplexing the first pulsed light, and by multiplexing the pulsed lights, a second delay multiplexer configured to produce a fourth pulsed light by providing a second delay time between two pulsed lights acquired by demultiplexing the second pulsed light, and by multiplexing the pulsed lights acquired from the second pulsed light, a detector configured to detect a pulsed light acquired by multiplexing the third pulsed light and the fourth pulsed light, an information acquirer configured to acquire information of a timing difference between the third pulsed light and the fourth pulsed light by performing synchronous detection on an output from the detector, and a period adjuster configured to adjust at least one of the first and second periods based on the information acquired by the information acquirer.

Further features and aspects of the present invention will become apparent from the following description of exemplary embodiments with reference to the attached drawings.

Advantageous Effects of Invention

The present invention provides a pulsed light synchronizer and a microscope system that can reliably operate.

DESCRIPTION OF EMBODIMENTS

Figure 1:
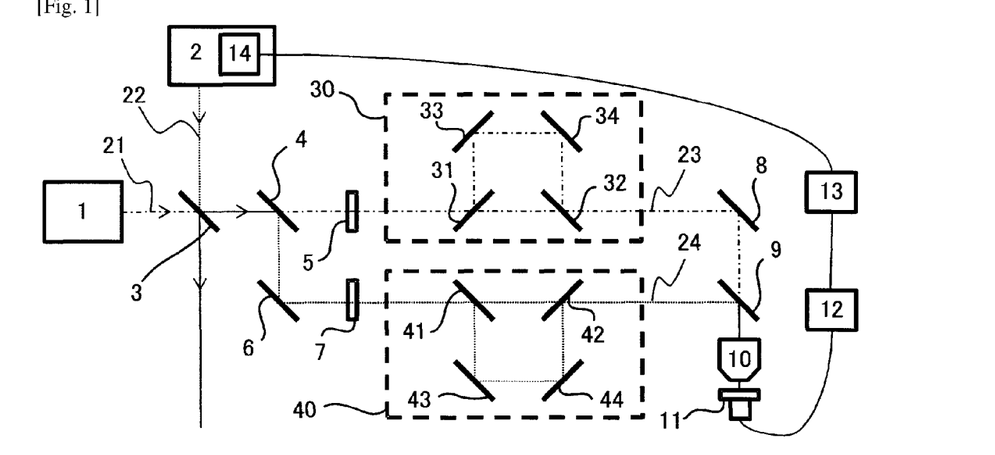
FIG. 1 is an optical path diagram of a pulsed light synchronizer according to an embodiment of the present invention.

FIG. 1 is an optical path diagram of a pulsed light (train) synchronizer (hereinafter, simply referred to as a "synchronizer") according to an embodiment of the present invention. The synchronizer synchronizes a first pulsed light 21 emitted by a pulsed laser (first pulsed laser) 1 and a second pulsed light 22 emitted by a pulsed laser (second pulsed laser different from the first pulsed laser) 2. Specifically, the synchronizer synchronizes timings of the emissions of the first pulsed light 21 and the second pulsed light 22 or keeps constant a difference therebetween. The first pulsed light 21 and the second pulsed light 22 have wavelengths λ1 and λ2 different from each other, respectively.

The pulsed laser 2, whose cavity length is variable, can adjust the pulse period (second period) of the second pulsed light 22. The pulsed laser 2 adjusts the second period depending on any timing shift between pulses so that the second period is synchronized with the pulse period (first period) of the first pulsed light 21, thereby synchronizing the timings of the pulses. This produces the first pulsed light on the first period, and produces the second pulsed light on the first period.

A half-mirror 3 transmits part of incident light, and reflects the remaining (part) of the incident light. The half-mirror 3 receives a light beam from the pulsed laser 1, transmitting part of the light beam in the right direction in FIG. 1 and reflecting the remaining thereof in the downward direction in FIG. 1. The half-mirror 3 receives a light beam from the pulsed laser 2, transmitting part of the light beam in the downward direction and reflecting the remaining in the right direction. The half-mirror 3 is disposed so that light beams from the pulsed lasers 1 and 2 are each divided into the two directions, in each of which divided light beams from the pulsed lasers 1 and 2 are multiplexed on the same axis. One pair of divided light beams are used in the synchronizer, and the other pair of divided light beams are used in a system, such as a nonlinear optical microscope, which requires synchronized pulsed lights.

A half-mirror 4 is a beam splitter that receives light from the half-mirror 3, transmitting the first pulsed light 21 and reflecting the second pulsed light 22. The half-mirror 4 is provided with a dielectric multilayer film designed to transmit light having the wavelength λ1 and to reflect light having the wavelength λ2.

A light intensity adjuster 5 receives the first pulsed light 21 transmitted through the half-mirror 4, and adjusts the light intensity of the first pulsed light 21. A method of the adjustment will be described later. After transmitted through the light intensity adjuster 5, the first pulsed light 21 enters a delay multiplexer 30.

A deflecting mirror 6 bends (deflects), by 90 degrees, the optical path of the second pulsed light 22 reflected by the half-mirror 4. A light intensity adjuster 7 receives the second pulsed light 22 whose optical path is bent by the deflecting mirror 6, and adjusts the light intensity of the second pulsed light 22. A method of the adjustment will be described later. After transmitted through the light intensity adjuster 7, the second pulsed light 22 enters a delay multiplexer 40.

The delay multiplexer (first delay multiplexer) 30 includes polarizing beam splitters (PBSs) 31 and 32 and mirrors 33 and 34. The PBSs each split incident light depending on a polarization component thereof, for example, transmitting the P-polarized component of the incident light and separating the S-polarized component of the incident light into a direction orthogonal to the direction of the incident light.

Light entering the PBS 31 is divided into two pulsed lights having polarization states orthogonal to each other and traveling in two different directions. One of the divided pulsed lights enters the PBS 32, and the other pulsed light is reflected by the mirrors 33 and 34 and then enters the PBS 32. The PBSs 31 and 32 and the mirrors 33 and 34 are disposed at such angles that two pulsed lights emitted from the PBS 32 are on the same axis. A pulsed light multiplexed through the PBS 32 is referred to as a third pulsed light 23.

Figure 2A:
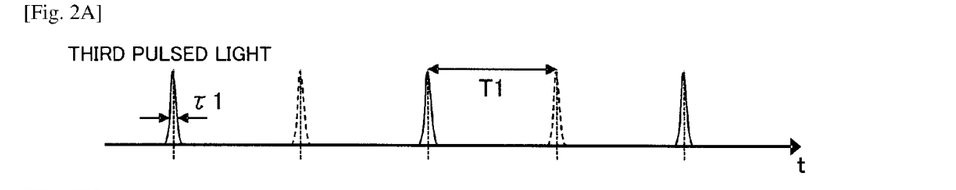
FIG. 2A illustrates a time profile of the intensity of a third pulsed light in the pulsed light synchronizer illustrated in FIG. 1.

FIG. 2A illustrates a time profile of the intensity of the third pulsed light 23. In FIG. 2A, the horizontal axis represents time (t), and the vertical axis represents the light intensity, and this arrangement is also applied in FIGS. 2B to 2G.

FIG. 2A illustrates pulses due to the two pulsed lights divided through the PBS 31, respectively with a solid line and a dotted line. Since the two divided pulsed lights travel on optical paths having lengths different from each other, the pulses illustrated with the solid line and the dotted line have a time shift therebetween by a first delay time T1. The light intensity adjuster 5 adjusts the polarization of the first pulsed light 21 so that the pulsed lights illustrated with the solid line and the dotted line have equal intensities. The light intensity adjuster 5 is, for example, a half-wave plate, and adjusts an intensity ratio of the pulsed lights divided through the PBS 31 by rotating the direction of the polarization entering the delay multiplexer 30.

Typically, once performed, the adjustment of the light intensity adjuster 5 does not need to be performed constantly, unlike feedback control. For example, to acquire the information illustrated in FIG. 2A, a dedicated photodetector is placed at a position at which a deflecting mirror 8 is to be installed, and the light intensity of at least one of the two divided pulsed lights is adjusted so that the two divided pulsed lights have equal light intensities after multiplexed. For example, the half-wave plate may be rotated around an optical axis illustrated with a dashed and single-dotted line in FIG. 1 so that two adjacent pulses have equal light intensities. The half-wave plate may be rotated manually by a maintainer so that two adjacent pulses have equal light intensities, or a rotator of the half-wave plate may be controlled by an unillustrated controller so that two adjacent pulses have equal light intensities. Alternatively, depending on the sensitivity of a detector (photodetector) 11 described later, power supply to the pulsed laser 2 may be cut or the second pulsed light 22 may be shielded, and the half-wave plate may be rotated around the optical axis so that an output from a synchronous detection circuit 12 described later is zero.

The PBSs 31 and 32 may be each replaced with a half-mirror that equally divides the light intensity of incident light. In this case, in place of the light intensity adjuster 5, an element (variable ND filter, for example) that adjusts the light intensity is introduced into one of optical paths bifurcating at the half-mirror.

Similarly, the delay multiplexer (second delay multiplexer) 40 includes PBSs 41 and 42 and mirrors 43 and 44. Light entering the PBS 41 is divided into two pulsed lights having polarization states orthogonal to each other and traveling in two different directions. One of the divided pulsed lights enters the PBS 42, and the other pulsed light is reflected by the mirrors 43 and 44 and then enters the PBS 42. The PBSs 41 and 42 and the mirrors 43 and 44 are disposed at such angles that so that two pulsed lights emitted from the PBS 42 are on the same axis. A pulsed light multiplexed through the PBS 42 is referred to as a fourth pulsed light 24.

Figure 2B:
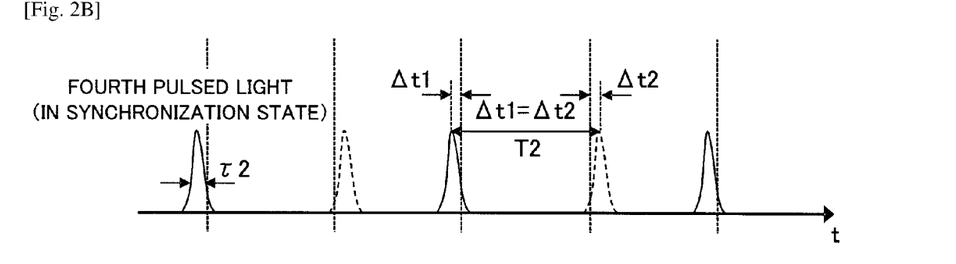
FIG. 2B illustrates a time profile of the intensity of a fourth pulsed light in the pulsed light synchronizer illustrated in FIG. 1.

FIG. 2B illustrates a time profile of the intensity of the fourth pulsed light 24. FIG. 2B illustrates pulses due to the two pulsed lights divided through the PBS 41 respectively with a solid line and a dotted line. Since the two divided pulsed lights travel on optical paths having lengths different to each other, the pulses illustrated with the solid line and the dotted line have a time shift therebetween by a second delay time T2. The second delay time T2 has such a relationship with the first delay time T1 that is represented by Expression (1). The light intensity adjuster 7 adjusts the polarization of the second pulsed light 22 so that the pulsed lights illustrated with the solid line and the dotted line have equal intensities. The light intensity adjuster 7 is, for example, a half-wave plate, and adjusts an intensity ratio of the pulsed lights divided through the PBS 41 by rotating the direction of the polarization entering the delay multiplexer 40.

Typically, once performed, the adjustment of the light intensity adjuster 7 does not need to be performed constantly, unlike feedback control. For example, to acquire the information illustrated in FIG. 2B, a dedicated photodetector is placed at a position at which a half-mirror 9 is to be installed. Then, the light intensity of at least one of the two divided pulsed lights is adjusted so that the two divided pulsed lights have equal light intensities after multiplexed. For example, the half-wave plate is rotated around an optical axis illustrated with a dotted line in FIG. 1 so that two adjacent pulses have equal light intensities. The half-wave plate may be rotated manually by a maintainer so that two adjacent pulses have equal light intensities, or a rotator of the half-wave plate may be controlled by an unillustrated controller so that two adjacent pulses have equal light intensities. Alternatively, depending on the sensitivity of the photodetector 11 described later, power supply to the pulsed laser 1 may be cut or the first pulsed light 21 may be shielded, and the half-wave plate may be rotated around the optical axis so that an output from the synchronous detection circuit 12 described later is zero.

The PBSs 41 and 42 may be each replaced with a half-mirror that equally divides the light intensity of incident light. In this case, in place of the light intensity adjuster 7, an element (variable ND filter, for example) that adjusts the light intensity is introduced on one of optical paths bifurcating at the half-mirror.

The third pulsed light 23 emitted from the delay multiplexer 30 is reflected by the deflecting mirror 8 so that the optical path of the third pulsed light 23 is bent by 90 degrees, and then enters the half-mirror 9. The third pulsed light 23 emitted from the delay multiplexer 30 and the fourth pulsed light 24 emitted from the delay multiplexer 40 are multiplexed on the same axis through the half-mirror 9. The half-mirror 9 has the same design as that of the half-mirror 4, and transmits light having the wavelength λ1 and reflects light having the wavelength λ2.

The third pulsed light 23 and the fourth pulsed light 24 that are multiplexed are focused on a light-receiving surface of the photodetector 11 through an objective lens 10. The objective lens 10 may have a numerical aperture of 0.5 or higher to obtain a large two-photon absorption signal detected at the photodetector 11.

The photodetector 11 includes, for example, a photodiode that receives the third pulsed light and the fourth pulsed light. The photodetector 11 converts a current produced through two-photon absorption at the light-receiving surface of the photodiode into a voltage. To obtain a two-photon absorption signal, the photodiode included in the photodetector 11 has sensitivity at a wavelength $\lambda 1 \cdot \lambda 2/(\lambda 1+\lambda 2)$ corresponding to a sum of photon energy ($E3 \propto 1/\lambda 1$) of the third pulsed light 23 and photon energy ($E4 \propto 1/\lambda 2$) of the fourth pulsed light 24, that is, E3+E4. When the third pulsed light 23 has a wavelength of 800 nm and the fourth pulsed light 24 has a wavelength of 1030 nm, a sensitivity for light detection needs to be at 450 nm.

Figure 2C:
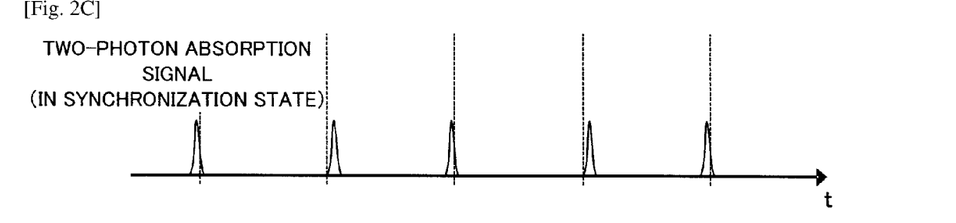
FIG. 2C illustrates a time profile of the intensity of two-photon absorption caused by the third and fourth pulsed lights in the pulsed light synchronizer illustrated in FIG. 1.

FIG. 2C illustrates a time profile of the two-photon absorption signal (current produced by the photodiode) corresponding to E3+E4 when the third pulsed light 23 is in the state illustrated in FIG. 2A and the fourth pulsed light 24 is in the state illustrated in FIG. 2B. The two-photon absorption signal is proportional to the product of the pulse intensity of the third pulsed light 23 and the pulse intensity of the fourth pulsed light 24.

FIGS. 2A and 2B each illustrate a state in which the pulsed lights are synchronized, and a timing difference between pulse peaks of the third pulsed light 23 and the fourth pulsed light 24 is equal between adjacent pulses (Δt1 and Δt2 in FIG. 2B are equal). This pulse synchronization state is achieved by controlling a pulse period adjuster 14 (or the cavity length of the pulsed laser 2) such that intensities of adjacent pulses of the two-photon absorption signal are equal as illustrated in FIG. 2C.

Figure 2D:
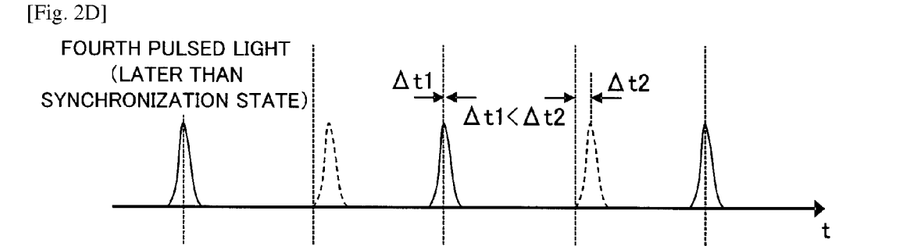
FIG. 2D illustrates a time profile of the intensity of the fourth pulsed light in the pulsed light synchronizer illustrated in FIG. 1.

FIG. 2D illustrates a time profile of the intensity of the fourth pulsed light 24 when the cavity length of the pulsed laser 1 or 2 has changed due to disturbance, and the fourth pulsed light 24 has reached the photodetector 11 later than the fourth pulsed light 24 in the pulse synchronization state.

Figure 2E:
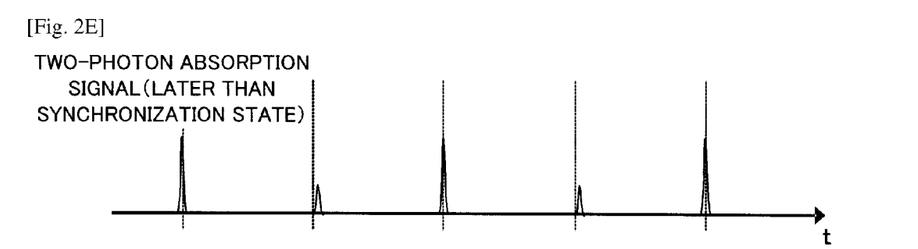
FIG. 2E illustrates a time profile of the intensity of the two-photon absorption caused by the third and fourth pulsed lights in the pulsed light synchronizer illustrated in FIG. 1.

FIG. 2E illustrates a time profile of the two-photon absorption signal corresponding to E3+E4 when the third pulsed light 23 and the fourth pulsed light 24 are respectively in the states illustrated in FIG. 2A and FIG. 2D. In this case, adjacent pulses of the two-photon absorption signal have different intensities.

Figure 2F:
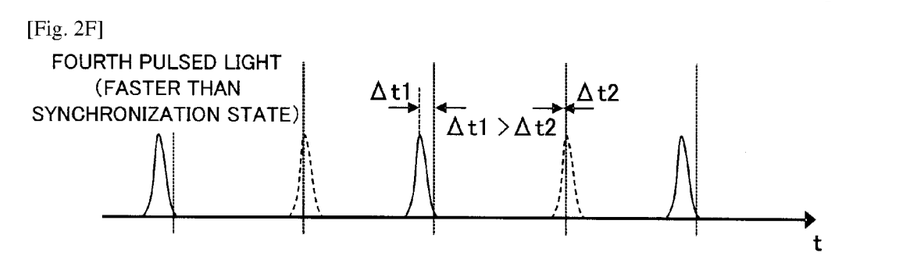
FIG. 2F illustrates a time profile of the intensity of the fourth pulsed light in the pulsed light synchronizer illustrated in FIG. 1.

FIG. 2F illustrates a time profile of the intensity of the fourth pulsed light 24 when the cavity length of the pulsed laser 1 or 2 has changed due to disturbance, and the fourth pulsed light 24 has reached at the photodetector 11 faster than the fourth pulsed light 24 in the pulse synchronization state.

Figure 2G:
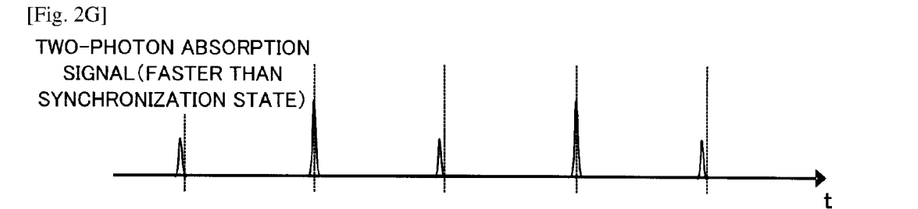
FIG. 2G illustrates a time profile of the intensity of the two-photon absorption caused by the third and fourth pulsed lights in the pulsed light synchronizer illustrated in FIG. 1.

FIG. 2G illustrates a time profile of the two-photon absorption signal corresponding to E3+E4 when the third pulsed light 23 and the fourth pulsed light 24 are respectively in the states illustrated in FIG. 2A and FIG. 2F. Similarly to FIG. 2E, adjacent pulses of the two-photon absorption signal have different intensities, but the intensities are inverted between FIG. 2E and FIG. 2F. Delay and advance of a pulsed light can be known by detecting this inversion of the intensities.

The photodetector 11 may include a nonlinear crystal (barium borate crystal, for example) that receives the third pulsed light 23 and the fourth pulsed light 24, and a photomultiplier that detects a sum frequency light produced through the nonlinear crystal. Similarly to the two-photon absorption signal corresponding to E3+E4, the sum frequency light has an intensity difference indicating the delay and advance of a pulsed light.

The intensity difference between adjacent pulses of the two-photon absorption signal is evaluated through synchronous detection described later, and thus the first delay time T1 and the second delay time T2 are set to be approximately half of the first (or second) pulse period. When a difference between T1 and T2 is zero, that is, when T1 and T2 are equal to each other, the delay and advance of a pulsed light cannot be evaluated because the intensity difference between adjacent pulses of a signal of interest is zero. When an absolute value of the difference between T1 and T2 is larger than a sum (T1+T2) of first and second pulse durations, the two-photon absorption signal is small and the intensity difference between adjacent pulses cannot be evaluated. Thus, the absolute value of the difference between T1 and T2 is required to be non-zero and smaller than or equal to the sum (τ1+τ2) of the first and second pulse durations. This requirement is equivalent to satisfying a condition below.

$$0<|T1-T2|\leq(\tau1+\tau2) \quad (1)$$

The first pulse duration is a full width at half maximum (half width) of each light pulse of the first pulsed light. The second pulse duration is a full width at half maximum of each light pulse of the second pulsed light. When the pulse synchronizer according to the embodiment of the present invention is reliably operated, each of the pulse durations may be approximately one to three times as large as the full width at half maximum.

T1 can be adjusted by changing the positions of the mirrors 33 and 34, and T2 can be adjusted by changing the positions of the mirrors 43 and 44. The intensity difference of the two-photon absorption signal has a period equal to the pulse period (second period) of the second pulsed light from which the fourth pulsed light is produced.

The synchronous detection circuit (information acquirer) 12 is an electric circuit such as a lock-in amplifier. The synchronous detection circuit 12 acquires, though synchronous detection, information of the amplitude on the second period (information of a timing difference between the third pulsed light and the fourth pulsed light), which is included in the output voltage of the photodetector 11, and outputs the information as a voltage. Since the second period and the first period are substantially equal to each other (completely synchronized through pulse synchronization), the synchronous detection circuit 12 may be configured to acquire information of only the amplitude of the first period (instead of the second period) from the output voltage of the photodetector 11.

The product of an input signal (sin α) and a reference signal (sin β) having the same frequency and phase as those of the input signal yields sin α·sin β={cos(α−β)−cos (α+β)}/2 using the trigometric identity, which is then written as {cos(0)−cos(2α)}/2 because α=β is established. This includes a direct current component proportional to the amplitude of the input signal and an alternate current component having a frequency twice as that of the input signal, and thus the direct current component for the input signal is obtained by removing the alternate current component through a lowpass filter.

Figure 3:
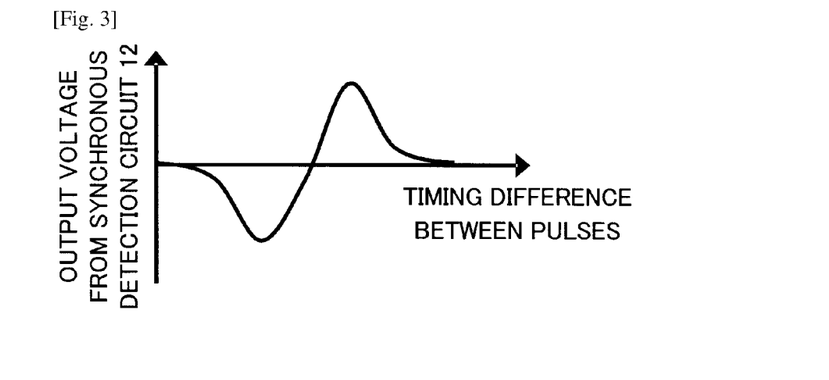
FIG. 3 illustrates a relationship between an output voltage from a synchronous detection circuit and a timing difference between pulses.

FIG. 3 is a graph illustrating a relationship between the output voltage (vertical axis) of the synchronous detection circuit 12, and a timing shift (horizontal axis) of the fourth pulsed light 24 from the fourth pulsed light in the pulse synchronization state (that is, a timing difference between the third pulsed light 23 and the fourth pulsed light 24).

The direction (delay or advance of the fourth pulsed light 24) of the timing difference between pulses corresponds to the sign of the output voltage of the synchronous detection circuit 12. The output voltage of the photodetector 11 includes, in addition to a component due to the two-photon absorption corresponding to E3+E4, components due to two-photon absorption in the third and fourth pulsed lights themselves such as E3+E3 and E4+E4, and components due to one-photon absorption such as E3 and E4. However, the components other than the component corresponding to E3+E4 are each produced on a period half of the second period, and thus do not affect the output from the synchronous detection circuit 12. The light intensity ratio of adjacent pulses illustrated in FIG. 2C corresponds to an intersection point (where the output voltage is zero) in FIG. 3, and the light intensity ratio of adjacent pulses illustrated in FIGS. 2E and 2G corresponds to regions in which the output voltage is positive and negative in FIG. 3.

A feedback circuit 13 outputs a voltage to be applied to the pulse period adjuster 14 installed in the pulsed laser 2 to correct a timing difference between pulses corresponding to the output voltage of the synchronous detection circuit 12.

When the output voltage of the synchronous detection circuit 12 is positive, for example, the fourth pulsed light 24 is assumed to be later than the third pulsed light 23. In this case, the feedback circuit 13 outputs a voltage for reducing the cavity length of the pulsed laser 2 to advance the fourth pulsed light 24 so that the fourth pulsed light 24 can be closer to the synchronization state. When the output voltage of the synchronous detection circuit 12 is negative, the feedback circuit 13 outputs a voltage for increasing the cavity length. These processes are such a feedback control that the output voltage of the synchronous detection circuit 12 is made zero, and can achieve the pulse synchronization state illustrated in FIGS. 2A and 2B. The feedback circuit 13 may be configured such that the output voltage of the synchronous detection circuit 12 is non-zero, so as to give a desired timing difference between the third pulsed light 23 and the fourth pulsed light 24.

The pulse period adjuster 14 includes a stage to which a phase modulator or mirror is attached, and the cavity length of the pulsed laser 2 is adjusted by applying a voltage to the phase modulator and driving the stage. The pulse period adjuster 14 may be installed not in the pulsed laser 2 but in the pulsed laser 1 so as to adjust the cavity length of the pulsed laser 1.

The third pulsed light 23 and the fourth pulsed light 24 are synchronized to be respectively in the states illustrated in FIGS. 2A and 2B at the light-receiving surface of the photodetector 11. Before synchronized, timings of pulse peaks of the third pulsed light 23 and the fourth pulsed light 24 are slightly shifted from each other at the light-receiving surface of the photodetector 11. In light beams divided through the half-mirror 3 and used in, for example, a nonlinear optical microscope, peaks of the first and second pulsed lights can be synchronized by adjusting the optical path length from the half-mirror 3 to the photodetector 11 to be different between the third and fourth pulsed lights so as to correct the shift.

The sign of the output voltage of the synchronous detection circuit 12 tells whether the third pulsed light 23 is delayed or advanced relative to the fourth pulsed light 24. When light intensities and pulse durations change, only the absolute value of the output voltage of the synchronous detection circuit 12 changes and the sign thereof does not change, and thus pulsed light (train) synchronization is achieved. Similarly, when wavelengths change in the range of the sensitivity of the photodetector 11, the pulsed light synchronization is achieved. Since only one photodetector is used, two photodetectors does not need to have identical arrangements relative to the objective lens unlike PLT 2.

In this embodiment, pulsed lights are each divided through the half-mirror 4 into pulsed lights having two wavelengths after multiplexed through the half-mirror 3, but the first and second pulsed lights may be each divided through a half-mirror before multiplexed through the half-mirror 3. In this embodiment, the delay multiplexer 30 and the delay multiplexer 40 assumes the use of light propagating in space, but may use light propagating in an optical fibre.

Figure 4:
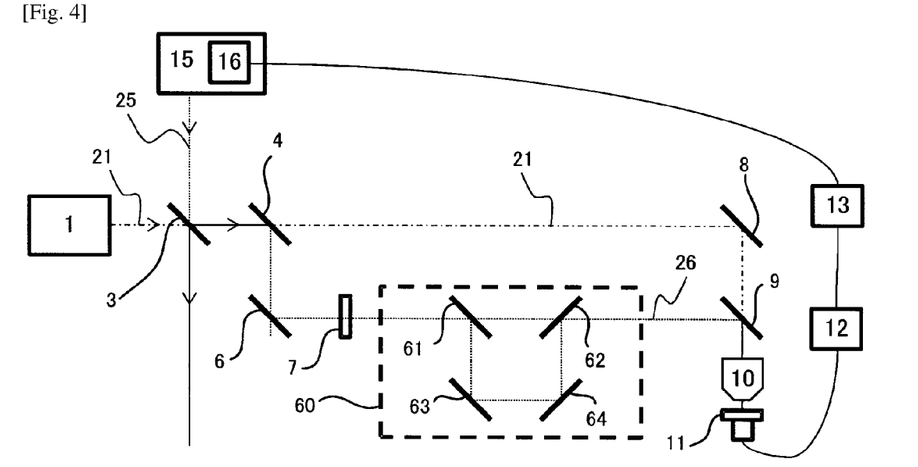
FIG. 4 is a block diagram of a variation of the pulsed light synchronizer illustrated in FIG. 1.

In this embodiment, the pulse periods of the two pulsed lights have a ratio of 1:1, but may have a ratio of 1:2. In other words, the second pulsed light may be produced on a period twice as that of the first period. FIG. 4 is a block diagram of the synchronizer when the pulse periods of the two pulsed lights have a ratio of 1:2. In a configuration illustrated in FIG. 4, timings of pulses are synchronized for the first pulsed light 21 and a second pulsed light 25 produced by a pulsed laser 15 and having a third pulse duration T3 and a third pulse period. The configuration is largely different from the configuration illustrated in FIG. 1 in that only one, instead of two, delay multiplexer is employed, and only the second pulsed light 25 is transmitted through the delay multiplexer.

Figure 5A:
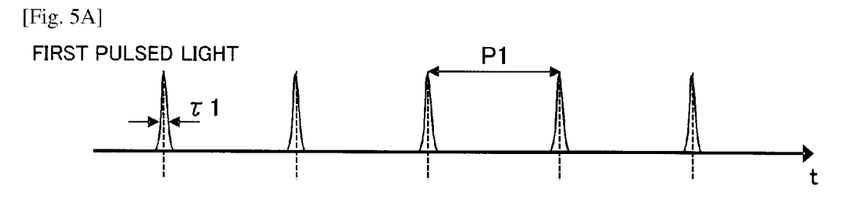
FIG. 5A illustrates a time profile of the intensity of a first pulsed light when the pulsed light synchronizer has the configuration illustrated in FIG. 4.

The first pulsed light 21 transmitted through the half-mirror 4 is reflected by the deflecting mirror 8 without being transmitted through a delay multiplexer, and then enters the half-mirror 9. FIG. 5A illustrates a time profile of the intensity of the first pulsed light 21 at the light-receiving surface of the photodetector 11. The first pulsed light 21 has a pulse period P1. In FIG. 5A, the horizontal axis represents time (t), and the vertical axis represents the light intensity, and this arrangement is also applied in FIG. 5B.

The second pulsed light 25 reflected by the half-mirror 4 is reflected by the deflecting mirror 6, transmitted through the light intensity adjuster 7, and enters a delay multiplexer 60. The delay multiplexer 60 includes PBSs 61 and 62 and mirrors 63 and 64. Light entering the PBS 61 is divided into two pulsed lights having polarization states orthogonal to each other and traveling in two different directions. One of the divided pulsed lights enters the PBS 62, and the other pulsed light is reflected by the mirrors 63 and 64, and then enters the PBS 62. The PBSs 61 and 62 and the mirrors 63 and 64 are disposed at such angles that two pulsed lights emitted from the PBS 62 are on the same axis.

Figure 5B:
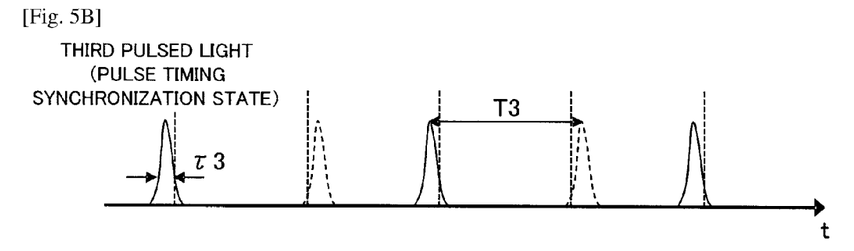
FIG. 5B illustrates a time profile of the intensity of the third pulsed light when the pulsed light synchronizer has the configuration illustrated in FIG. 4.

The pulsed lights multiplexed through the PBS 62 are referred to as a third pulsed light 26. FIG. 5B illustrates a time profile of the intensity of the third pulsed light 26 at the light-receiving surface of the photodetector 11, and pulses due to the two pulsed lights divided through the PBS 61 respectively with a solid line and a dotted line. Since the two divided pulsed lights travel on optical paths having lengths different to each other, the pulses illustrated with the solid line and the dotted line have a time shift therebetween by a third delay time T3.

The absolute value of a difference between the pulse period P1 of the first pulsed light 21 and the third delay time T3 is set to be non-zero and smaller than or equal to the sum of the first and third pulse durations ($\tau 1 + \tau 3$). This is equivalent to satisfying a condition below.

$$0 < |P1 - T3| \le (\tau 1 + \tau 3) \quad (2)$$

The first pulse duration $\tau 1$ is equal to the full width at half maximum (half width) of each pulse of the first pulsed light 21. The third pulse duration $\tau 3$ is equal to the full width at half maximum (half width) of each pulse of the second pulsed light 25. When the pulse synchronizer according to the embodiment of the present invention is reliably operated, each of the pulse durations may be approximately one to three times as large as the full width at half maximum.

Typically, once performed, the adjustment of the light intensity adjuster 7 does not need to be performed constantly, unlike feedback control. For example, to acquire the information illustrated in FIG. 5B, a dedicated photodetector is placed at a position at which the half-mirror 9 is to be installed. Then, the light intensity of at least one of the two divided pulsed lights is adjusted so that the two divided pulsed lights have equal light intensities after multiplexed. For example, the half-wave plate is rotated around an optical axis illustrated with a dotted line in FIG. 4 so that two adjacent pulses have equal light intensities. The half-wave plate may be rotated manually by a maintainer so that two adjacent pulses have equal light intensities, or a rotator of the half-wave plate may be controlled by an unillustrated controller so that two adjacent pulses have equal light intensities. Alternatively, depending on the sensitivity of the photodetector 11, power supply to the pulsed laser 1 may be cut, the first pulsed light 21 may be shielded, and the half-wave plate may be rotated around the optical axis so that an output from the synchronous detection circuit 12 described later is zero.

The first pulsed light 21 and the third pulsed light 26 multiplexed through the half-mirror 9 are focused on the light-receiving surface of the photodetector 11 through the objective lens 10. The synchronous detection circuit 12 acquires the amplitude (information of a timing difference between the first pulsed light and the third pulsed light) of the third pulse period component included in an output voltage of the photodetector 11, and outputs the amplitude as voltage. The output voltage of the synchronous detection circuit 12 reflects a pulse timing difference between the first pulsed light 21 and the third pulsed light 26. To correct the pulse timing difference, the feedback circuit 13 outputs the voltage to a pulse period adjuster 16, so that the first pulsed light 21 and the third pulsed light 26 are controlled to be in the states illustrated in FIGS. 5A and 5B, respectively.

The present invention is also applicable to a pulsed light synchronizer for two pulsed lights having pulse periods whose ratio is m:n. m and n are reduced integers. When m and n are both odd, similarly to the case in which the pulse periods are 1:1, a delay multiplexer is provided for each pulsed light. Similarly to the case in which the pulse periods are 1:1, the pulses can be synchronized by setting a delay time so that a time difference between the pulsed lights produced with delay is not larger than the sum of the widths of the pulses.

When m and n are a combination of an odd number and an even number, similarly to the case in which the pulse periods are 1:2, a delay multiplexer is provided only for the pulsed light for the odd number m or n. Similarly to the case in which the pulse periods are 1:2, the pulses can be synchronized by setting a delay time so that a time difference between the pulsed light produced with delay and the other pulsed light for which no delay multiplexer is provided is not larger than the sum of the widths of the pulses.

Embodiment 1

Figure 6:
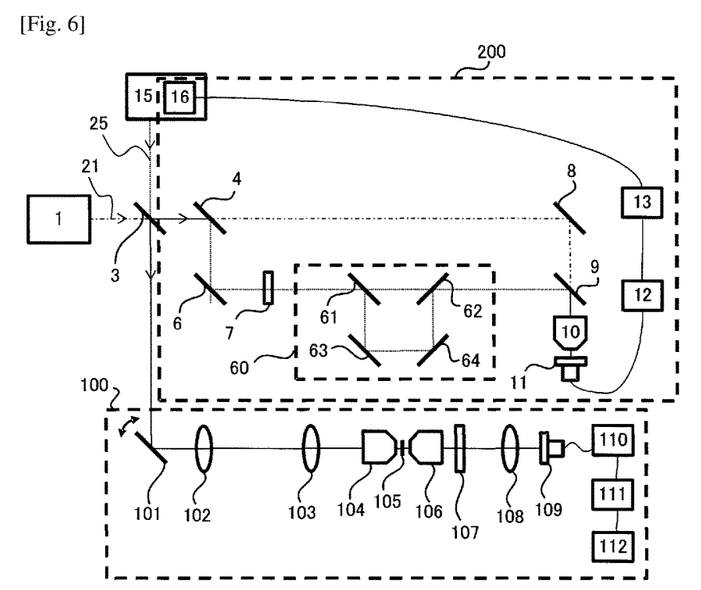
FIG. 6 is a conceptual diagram of an SRS microscope using the pulsed light synchronizer illustrated in FIG. 4 according to Embodiment 1.

FIG. 6 is a block diagram of a microscope system according to Embodiment 1 of the present invention. The microscope system includes an SRS microscope 100 and a pulsed light synchronizer 200. The SRS microscope 100 multiplexes two pulsed lights emitted from the two pulsed lasers 1 and 15 and having different wavelengths and detects stimulated Raman scattering (SRS) light produced by focusing and simultaneously emitting the pulses on a sample 105. Thus, the SRS microscope 100 is a nonlinear optical microscope that irradiates the sample with the two pulsed lights emitted from the two pulsed lasers and having different wavelengths, and observes the sample through a nonlinear optical process. The pulsed light synchronizer 200 synchronizes pulsed lights emitted from the two pulsed lasers 1 and 15.

The SRS is a nonlinear optical phenomenon that occurs proportionally to the product of the intensities of lights having the different wavelengths. To efficiently produce the SRS, laser light beams having two wavelengths are focused at an identical position, and pulsed lights having the two wavelengths are synchronized so that the pulsed lights are simultaneously focused. When the SRS is produced, among the pulsed lights having the two wavelengths, the intensity of the pulsed light having a shorter wavelength is reduced, and the intensity of the pulsed light having a longer wavelength is increased. To efficiently produce the SRS, a pulsed laser having a pulse duration of 1 to 10 picoseconds is desirably used.

Figure 7A:
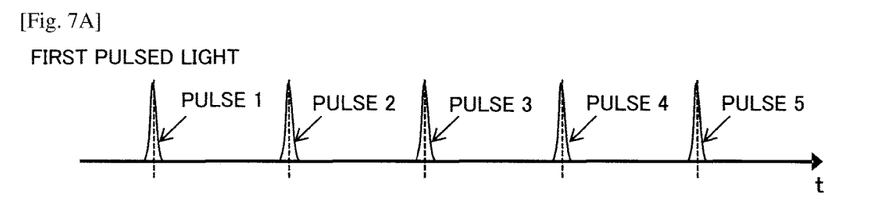
FIG. 7A illustrates a time profile of the intensity of a first pulsed light in the SRS microscope.
Figure 7B:
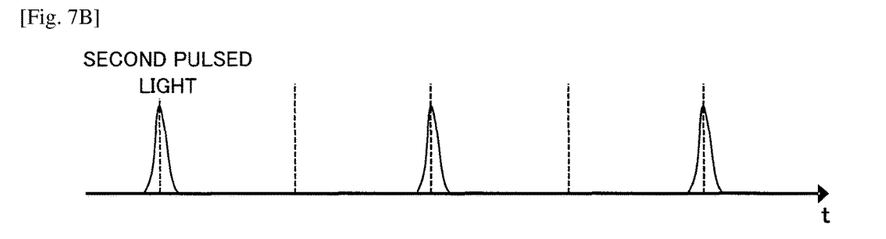
FIG. 7B illustrates a time profile of the intensity of a second pulsed light in the SRS microscope.

The pulsed lasers 1 and 15 produce pulsed lights whose pulse periods are 1:2. FIG. 7A illustrates the first pulsed light 21 produced by the pulsed laser 1, and FIG. 7B illustrates the second pulsed light 25 produced by the pulsed laser 15. In FIGS. 7A and 7B, the horizontal axis represents time (t), and the vertical axis represents the light intensity. The wavelength ($\lambda 1$) of the first pulsed light 21 is smaller than the wavelength ($\lambda 2$) of the second pulsed light 25.

A solid-state laser (titanium-sapphire laser) having a central wavelength of 800 nm and a pulse period of 12.5 nanoseconds is used as the pulsed laser 1. For example, Mai Tai, which is manufactured by Spectra-Physics, is used. A ytterbium-doped fibre laser having a central wavelength of 1030 nm and a pulse period of 25 nanoseconds is used as the pulsed laser 15.

When pulses of the first pulsed light 21 and the second pulsed light 25 are focused at an identical position on the sample at synchronized timings as illustrated in FIGS. 7A and 7B, the light intensity of a pulsed light transmitted through the sample by the SRS is changed. The light intensities of pulses 1, 3, and 5 in FIG. 7A are reduced, and the light intensities of pulses 2 and 4 are not changed. Since this difference between the light intensities of adjacent pulses is minute, the difference is detected through synchronous detection.

The detected difference between the light intensities corresponds to an SRS signal, and information of molecules at a position where the light beams are focused is reflected on the SRS signal. For example, when the resonance frequency of the molecular vibration at the position is equal to a difference between the light frequencies of the two lasers ($c/\lambda 1 - c/\lambda 2$), the SRS signal becomes large. c represents the speed of light. The Raman spectrum can be acquired by acquiring the SRS signal while the difference between the light frequencies of the two lasers ($c/\lambda 1 - c/\lambda 2$) is changed. The Raman spectrum allows estimation of what kinds of molecules are included in the sample. The SRS microscope can acquire a spectrum at the same level as that of a microscope exploiting spontaneous Raman scattering. Since the SRS has a scattering efficiency extremely larger than that of the spontaneous Raman scattering, the SRS microscope can acquire the Raman spectrum in a shorter time than the microscope exploiting the spontaneous Raman scattering. The wavelength of at least one of the two lasers is changed to obtain the Raman spectrum. Since the change of the wavelength changes the sensitivity of the photodetector, the microscope system of Embodiment 1, which reliably synchronizes pulsed lights irrespective of the change of the wavelength, is applicable as the SRS microscope.

The half-mirror 3 multiplexes light beams emitted from the pulsed lasers 1 and 15 onto the same axis, and divides the light beams in two directions. One of the divided light beams enters the pulsed light synchronizer 200, and the other enters the SRS microscope 100. The pulsed light synchronizer 200 synchronizes pulsed lights of two pulsed lasers entering the SRS microscope 100.

The SRS microscope 100 has a configuration of a laser scanning microscope. Light beams of the two pulsed lasers enter a beam scanner 101 on the same axis, and deflected and emitted by the beam scanner 101. The beam scanner 101 includes a galvano scanner and a resonant scanner, and changes the direction of the optical axis of the light beams into two directions orthogonal to each other. For simplification, FIG. 6 illustrates the two mirrors in the beam scanner 101 representatively as one mirror. The use of the resonant scanner (having a scanning frequency of 8 kHz) and the galvano scanner (having a scanning frequency of 15 Hz) allows an image of 500 lines to be acquired at 30 frames per second.

The light beams deflected by the beam scanner 101 enter an objective lens 104 though lenses 102 and 103. The lenses 102 and 103 disposed so that the beam scanner 101 and an entrance pupil of the objective lens 104 are conjugate with each other allow the light beams deflected through the beam scanner 101 to be focused on the sample 105 with their light being not shielded. The magnification of an optical system through the lenses 102 and 103 is selected so that the size of the entrance pupil of the objective lens 104 is equal to the size of the incident light beam. This minimizes the size of a light spot focused through the objective lens 104 and improves a spatial resolution of detecting the SRS signal. Since an increased intensity of the light spot enhances the SRS signal, leading to an improved signal-to-noise ratio (S/N ratio) of the detection of the SRS signal. The objective lens 104 desirably has a larger numerical aperture (NA) in terms of the spatial resolution of detecting the SRS signal and the S/N ratio.

The sample 105 is sandwiched between cover glasses (not illustrated) each having a thickness of several 10 s to 200 micrometers. Two-dimensional scanning of the light spot focused on the sample 105 is performed through the deflection of the light beams through the beam scanner 101, and produces the SRS signal as a two-dimensional image. Since the SRS signal is produced only at the focused light spot, a three-dimensional image can be obtained by moving the sample 105 on a stage (not illustrated) in the direction of the optical axis.

To thoroughly receive light transmitted through the sample 105 and provided with an intensity modulation through the SRS, the objective lens 106 has a numerical aperture (NA) equivalent to or higher than that of the objective lens 104. Light beams emitted from the objective lens 106 are transmitted through a filter 107 and a lens 108 and then made incident on the light-receiving surface of a photodiode 109. The filter 107 includes a dielectric multilayer film that shields light having the wavelength $\lambda 2$ and transmits light having the wavelength $\lambda 1$. The photodiode 109 is irradiated with the pulsed light that is emitted from the pulsed laser 1 and repeats the intensity modulation through the SRS at each pulse. A silicon photodiode having a sensitivity to a pulsed light of 800 nanometers and having a cutoff frequency of 40 MHz or higher is used as the photodiode 109.

The pulsed light 21 from the pulsed laser 1 has a repetition frequency of 80 MHz (on a pulse period of 12.5 nanoseconds), whereas the intensity modulation through the SRS has a repetition frequency of 40 MHz (on a period of 25 nanoseconds). A current-voltage converter 110 is an electric circuit for outputting, as a voltage signal, a current signal produced by the photodiode 109.

A synchronous detection circuit 111 extracts the amplitude of a component at 40 MHz from the voltage signal output from the current-voltage converter 110 and outputs the amplitude as a voltage. A mixer circuit or a lock-in amplifier is used as the synchronous detection circuit 111. The output voltage from the synchronous detection circuit 111 indicates the degree of the SRS at a focus point on the sample 105.

A computer 112 displays a two-dimensional image of output signals (SRS signals) of the synchronous detection circuit 111 that are acquired by using a signal for controlling the beam scanner 101. The computer 112 can also display a three-dimensional image of SRS signals acquired by moving the sample 105 on the stage (not illustrated) in the direction of the optical axis. The computer 112 can also display a Raman spectrum using SRS signals acquired by changing the wavelength of at least one of two pulsed lasers.

The present invention is also applicable to a pulsed light synchronization method of synchronizing the first pulsed light having the first pulse duration and the first period, and the second pulsed light having the second pulse duration and the second period equal to or twice as the first period. The pulsed light synchronization method may be realized as a program that causes a computer to execute steps.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-165643, filed on Aug. 18, 2014 which is hereby incorporated by reference herein in its entirety.

INDUSTRIAL APPLICABILITY

The present invention is applicable in coinciding timings of pulses of two pulsed lights emitted from two pulsed lasers.

REFERENCE SIGNS LIST

1 . . . pulsed laser (first pulsed laser), 2 and 15 . . . pulsed laser (second pulsed laser), 11 . . . photodetector, 12 . . . synchronous detection circuit (information acquirer), 30 . . . first delay multiplexer, 40 . . . second delay multiplexer, 200 . . . pulsed light synchronizer

The invention claimed is:

1. A pulsed light synchronizer configured to synchronize a first pulsed light produced on a first period and a second pulsed light produced on the first period with each other, the pulsed light synchronizer comprising:
a first delay multiplexer configured to produce a third pulsed light by providing a first delay time between two pulsed lights acquired by dividing the first pulsed light, and by multiplexing the pulsed lights acquired from the first pulsed light;
a second delay multiplexer configured to produce a fourth pulsed light by providing a second delay time between two pulsed lights acquired by dividing the second pulsed light, and by multiplexing the pulsed lights acquired from the second pulsed light;
a detector configured to detect a pulsed light acquired by multiplexing the third pulsed light and the fourth pulsed light;
an information acquirer configured to acquire information of a timing difference between the third pulsed light and the fourth pulsed light based on an output from the detector; and
a period adjuster configured to adjust at least one of the first and second periods based on the information acquired by the information acquirer.

2. The pulsed light synchronizer according to claim 1, wherein a condition below is satisfied:

$$0 < |T1 - T2| \le (\tau 1 + \tau 2)$$

where $\tau 1$ represents a pulse duration of the first pulsed light, $\tau 2$ represents a pulse duration of the second pulsed light, T1 represents the first delay time, and T2 represents the second delay time.

3. The pulsed light synchronizer according to claim 1, further comprising a light intensity adjuster configured to adjust at least one of light intensities of the two pulsed lights acquired through division so that the light intensities of the two pulsed lights thus adjusted can become equal to each other after being multiplexed in at least one of the first delay multiplexer and the second delay multiplexer.

4. The pulsed light synchronizer according to claim 1, wherein the detector includes a photodiode configured to receive the third pulsed light and the fourth pulsed light and to convert a current produced through two-photon absorption into a voltage at a light-receiving surface of the photodiode.

5. The pulsed light synchronizer according to claim 1, wherein the detector includes a nonlinear crystal configured to receive the third pulsed light and the fourth pulsed light, and a photomultiplier configured to detect a sum frequency light produced through the nonlinear crystal.

6. The pulsed light synchronizer according to claim 1, wherein the information acquirer is configured to acquire information of the timing difference between the third pulsed light and the fourth pulsed light by performing synchronous detection on an output from the detector.

7. A pulsed light synchronizer configured to synchronize a first pulsed light produced on a first period and a second pulsed light produced on a second period that is twice as long as the first period with each other, the pulsed light synchronizer comprising:
a delay multiplexer configured to produce a third pulsed light by providing a delay time between two pulsed lights acquired by dividing the second pulsed light, and by multiplexing the pulsed lights acquired from the first pulsed light;
a detector configured to detect a pulsed light acquired by multiplexing the first pulsed light and the third pulsed light;
an information acquirer configured to acquire information of a timing difference between the first pulsed light and the third pulsed light based on an output from the detector; and
a period adjuster configured to adjust at least one of the first and second periods based on the information acquired by the information acquirer.

8. The pulsed light synchronizer according to claim 7, wherein a condition below is satisfied:

$$0 < |P1 - T3| \le (\tau 1 + \tau 3)$$

where $\tau 1$ represents a pulse duration of the first pulsed light, $\tau 3$ represents a pulse duration of the second pulsed light, P1 represents the first period, and T3 represents the delay time.

9. The pulsed light synchronizer according to claim 7, further comprising a light intensity adjuster configured to adjust at least one of light intensities of the two pulsed lights acquired through division so that the light intensities of the two pulsed lights can become equal to each other after being multiplexed in the delay multiplexer.

10. The pulsed light synchronizer according to claim 7, wherein the detector includes a photodiode configured to receive the first pulsed light and the third pulsed light and to convert a current produced through two-photon absorption into a voltage at a light-receiving surface of the photodiode.

11. The pulsed light synchronizer according to claim 7, wherein the detector includes a nonlinear crystal configured to receive the first pulsed light and the third pulsed light, and a photomultiplier configured to detect a sum frequency light produced through the nonlinear crystal.

12. The pulsed light synchronizer according to claim 7, wherein the information acquirer is configured to acquire information of the timing difference between the first pulsed light and the third pulsed light by performing synchronous detection on an output from the detector.

13. A microscope system comprising:
the pulsed light synchronizer according to claim 1; and
a nonlinear optical microscope configured to irradiate a sample with the first and second pulsed lights and to observe the sample through a nonlinear optical process.

* * * * *